("12") United States Patent  (10) Patent No.: US 7,537,704 B2
Bode-Böger et al.  (45) Date of Patent: May 26, 2009

(54) METHOD FOR DETERMINING THE CONCENTRATION OF ASYMMETRIC DIMETHYLARGININE (ADMA)

(75) Inventors: Stefanie M. Bode-Böger, Laatzen (DE); Jens Martens-Lobenhoffer, Hamburg (DE)

(73) Assignees: Medizinische Fakultat der Otto-Von-Guericke-Universitat, Madgeburg (DE); ESA Patentverwertungsagentur Sachsen-Anhalt GmbH, Madgeburg (DE)

(\*) Notice: Subject to any disclaimer, the term of this patent is extended or adjusted under 35 U.S.C. 154(b) by 0 days.

(21) Appl. No.: 11/915,828

(22) PCT Filed: May 13, 2006

(86) PCT No.: PCT/DE2006/000829

§ 371 (c)(1),
(2), (4) Date: Jan. 30, 2008

(87) PCT Pub. No.: WO2006/128419

PCT Pub. Date: Dec. 7, 2006

(65) Prior Publication Data

US 2008/0199848 A1  Aug. 21, 2008

(30) Foreign Application Priority Data

May 28, 2005 (DE) .................... 10 2005 024 531
Nov. 26, 2005 (DE) .................... 10 2005 056 408

(51) Int. Cl.
    *B01D 15/08* (2006.01)
(52) U.S. Cl. .................. 210/656; 435/7.92; 436/86; 436/161
(58) Field of Classification Search .............. 210/635, 210/656, 198.2; 250/282; 435/7.92; 436/86, 436/161
See application file for complete search history.

(56) References Cited

U.S. PATENT DOCUMENTS 6,358,699 B1\* 3/2002 Balint et al. ................ 435/18

(Continued)

OTHER PUBLICATIONS

Google Abstract to provide publication date. (Undated).\*

(Continued)

*Primary Examiner*—Ernest G Therkorn
(74) *Attorney, Agent, or Firm*—Norris McLaughlin & Marcus, PA; Christa Hildebrand

(57) ABSTRACT

The invention relates to a method for determining the concentration of asymmetric dimethylarginine (ADMA) simultaneously with arginine and with symmetric dimethylarginine (SDMA) in biological samples by means of HPLC-MS-MS. The sample preparation consists exclusively of adding a solution of isotope-labeled internal standards ($^{13}C_6$-arginine and $D_6$-ADMA) and of adding a mixture consisting of acetonitrile/propionic acid/trifluoroacetic acid for precipitating high-molecular proteins, the quantity and composition being realized in such a manner that a bringing of the sample composition in line with the composition of the mobile phase in the HPLC separation is achieved without requiring a derivitization or extraction of the analytes. The chromatographic separation of the analytes ensues on a silica normal phase HPLC column while using a mobile phase consisting of water/acetonitrile/propionic acid/trifluoroacetic acid, the volume ratio of water to acetonitrile ranging from 2 to 98 to 30 to 70, the volume percent of trifluoroacetic acid ranging from 0.01 to 0.5, the volume percent of propionic acid being 10 to 100 times higher than trifluoroacetic acid, and the optimized composition of the mobile phase consists of acetonitrile/propionic acid/trifluoroacetic acid with 10/90/1/0.025 volume percents. The detection and quantification ensue by means of tandem mass spectrometry with the following fragmentations being observed: 175.2 m/z→70.1 m/z for arginine, 181.2 m/z→74.1 m/z for $^{13}C_6$-arginine, 203.2 m/z→172.1 m/z for SDMA, 203.2 m/z→46.1 m/z for ADMA and 209.2 m/z→70.1 m/z $D_6$-ADMA.

4 Claims, 3 Drawing Sheets

U.S. PATENT DOCUMENTS

| | | | |
|---|---|---|---|
| 6,720,188 B2* | 4/2004 | Kaddurah-Daouk et al. | 436/86 |
| 2002/0081626 A1* | 6/2002 | Kaddurah-Daouk et al. | 435/7.1 |
| 2004/0214252 A1* | 10/2004 | Lin et al. | 435/7.92 |
| 2006/0094122 A1* | 5/2006 | Boeger et al. | 436/90 |
| 2008/0073500 A1* | 3/2008 | Cerda | 250/282 |
| 2008/0199848 A1* | 8/2008 | Bode-Boger et al. | 435/4 |
| 2009/0053741 A1* | 2/2009 | Vallance et al. | 435/7.72 |

OTHER PUBLICATIONS

Key Y. Lin; Akira Ito, Tomoko Asagami, Philip S. Tsao, Shanthi Adimoolam, Masumi Kimoto, Hideaki Tsuji, Gerald M. Reaven and John P. Cooke, Impaired Nitric Oxide Synthase Pathway in Diabetes Mellitus, Circulation 2002, 106:987-992.

Hartmut Kirchherr and W. Nikolaus Kuhn-Velten, HPLC-Tandem Mass Spectrometric Method for Rapid Quantification of Dimethylarginines in Human Plasma, Clinical Chemistry 2005, 51:249-252.

Shlomo Pundak and Meir Wilchek, Synthesis of Guanidino-N-alkylarginines by the Use of Polymeric Pseudoureas, J. Org. Chem. 1981, 46, S. 808-809.

Ben-Mei Chen, Lin-Wei Xia and Rui-Qin Zhao, Determination of N(G), N(G)-dimethylargine in Human Plasma by High-Performance Liquid Chromatography, Journal of Chromatography B Biomed Sci App. 1997, 247:11-16.

Jens Meyer, Nadja Richter and Markus Hecker, High-Performance Liquid Chromatographic Determination of Nitric Oxide Synthase-Related Arginine Derivatives in Vitro and in Vivo, Analytical Biochemistry, 1997, 692:257-62.

Anders Pettersson, Lotta Uggla and Viveca Backman, Determination of Dimethylated Arginines in Human Plasma by High-Performance Liquid Chromatography, Biomed Science Applied 1997, 692:257-62.

Jingbo Pi, Yoshito Kumagai, Guifan Sun and Nobuhiro Shimojo, Improved Method for Simultaneous Determination of L-Arginine and its Mono and Dimethylated Metabolites in Biological Samples by High-Performance Liquid Chromatrography, Journal of Chromatography B Biomed,Science Applied 2000, 742:199-203.

Yasui Dobashi, Tomofumi Santa, Kazuya Nakagomi and Kazuhiro Imai, An Automated Analyzer for Methylated Arginines in Rat Plasma by High-Performance Liquid Chromatography with Post-Column Fluorescence Reaction, Analyst 2002, 127:54-9.

Tom Teerlink, Robert J. Nijveldt; Sigrid De Jong and Paul A.M Van Leeuwen, Determination of Arginine, Asymmetric Dimethylarginine, and Symmetric Dimethylarginine in Human Plasma and Other Biological Samples by High-Performance Liquid Chromatography, Analytical Biochemistry 2002, 303: 131-137.

Maurizio Marra, Anna Rita Bonfigli, Roberto Testa, Ivano Testa, Anna Gambini and Gilberto Coppa, High-Performance Liquid Chromatographic Assay of Asymmetric Dimethylarginine, Symmetric Dimethylarginine, Arginine in Human Plasma by Derivatization with Napthalene-2,3-Dicarboxaldehyde, Analytical Biochemistry 2003, 318, 13-7.

Tamila Heresztyn, Matthew I. Worthley and John D. Horowitz, Determination of L-Arginine and N(G), N(G)-and N(G), N(G')-Dimethyl-L-Arginine in Plasma by Liquid Chromatography as AccQ-Flour (TM) Fluorescent Derivatives, Journal of Chromatography B 2004, 805: 325-9.

Wei-Zheng Zhang and David M. Kaye, Simultaneous Determination of Arginine and Seven Metabolites in Plasma by Reversed-Phase Liquid Chromatography with a Time-Controlled Ortho-Phthaldialdehyde Precolumn Derivatization, Analytical Biochemistry 2004, 326: 87-92.

E. Causse, N. Siri, J. F. Arnal, C. Bayle, P. Malatray, P. Valdiguie, R. Salvayre and F. Couderc, Determination of Asymmetrical Dimethylarginine by Capillary Electrophoresis-Laser Induced Fluorescence, Journal of Chromatragraphy B 2000, 741:77-83.

Gabriele Trapp, Karsten Sydow, Maria T. Dulay, Tina Chou, John P. Cooke and Richard N. Zare, Capillary Electrophoretic and Micellar Electrokinetic Separations of Asymmetric Dimethyl-L-Arginine and Structurally Related Amino Acids: Quantitation in Human Plasma, J. Sep Sci. 2004, 27:1483-90.

Dimitrios Tsikas, Bibiana Schubert, Frank-Mathias Gutzki, Jorg Sandmann and Jurgen C. Frolich, Quantitative Determination of Circulating and Urinary Asymmetric Dimethylarginine (ADMA) in Humans by Gas Chromatography B Analytical Technology Biomed Life Science 2003, 798:87-99.

Jennifer Albsmeier, Edzard Schwedhelm, Friedrich Schulze, Mariola Kastner and Rainer H. Boger, Determination of N(G), N(G)-Dimethyl-L-Arginine, an Endogenous NO Synthase Inhibitor, by Gas Chromatography-Mass Spectrometry, Journal of Chromatography B Analytical Technology Biomed Life Science 2004, 809: 59-65.

Lan-Fang Huang, Fang-Qui Guo, Yi-Zeng Liang, Bo-Yang Li and Ben-Mei Cheng, Simultaneous Determination of L-Arginine and its Mono- and Dimethylated Metabolites in Human Plasma by High-Performance Liquid Chromatography-Mass Spectrometry, Anayltical Bioanal Chem 2004, 380:643-649.

Edzard Schwedhelm, Jing Tan-Andresen, Renke Maas, Ulrich Riederer, Friedrich Schulze and Rainer H. Bogger, Liquid Chromatography-Tandem Mass Spectrometry Method for the Analysis of Asymmetric Dimethylarginine in Human Plasma, Clinical Chemistry 2005, 51: 1268-1271.

Lan-Fang Huang, Fang-Qui Guo, Yi-Zeng Liang, Qian-Nan Hu and Ben-Mai Cheng, Rapid Simultaneous Determination of Arginine and Methylated Arginines in Human Urine by High-Performance Liquid Chromatography-Mass Spectrometry, Journal of Chromatography B 2000, vol. 487 S. 145-153.

Karthic Vishwanathan, Randall L. Tackett, James T. Stewart and Michael G. Bartlett, Determination of Arginine and Methylated Arginines in Human Plasma by Liquid Chromatography-Tandem Mass Spectrometry, Journal of Chromatography B, 2000, vol. 748 S, 157-166.

Jens Martens-Lobenhoffer and Stefanie M. Bode-Boger, Simultaneous Detection of Arginine, Asymmetric Dimethylarginine, Symmetric Dimethylarginine and Citrulline in Human Plasma and Urine Applying Liquid Chromatography-Mass Spectrometry with Very Straightforward Sample Preparation, Journal of Chromatography B, 2003, vol. 798, S. 231-239.

Wilson Z. Shou and Weng Naidong, Simple Means to Alleviate Sensitivity Loss by Trifluororacetic Acid (TFA) Mobile Phases in the Hydrophilic Interaction Chromatography-electrospray Tandem Mass Spectrometric (HILIC-ESI/MS/MS) Bioanalysis of Basic Compounds, Journal of Chromatography B 2005, vol. 825, S. 186-192.

Peter M. Gehrig, Peter E. Hunziker, Sotir Zaharieve and Sandor Ponger, Fragmentation Pathways of N(G) Methylated and Unmodified Arginine Residues in Peptides Studied by ESI-MS/MS and MALDI-MS, Journal of the American Society for Mass Spectrometry, Elsevier Inc., US Bd., 15, NR2, 2004, S. 142-149.

Edzard Schwedhelm, Quantification of ADMA: Analytical Approaches, Vascular Medicine, London 2005, Bd. 10, S. 89-95.

Jens Martens-Lobenhoffer and Stefanie M. Bode-Boger, Fast and Efficient Determination of Arginine, Symmetric Dimethylarginine, and Asymmetric Dimethylarginine in Biological Fluids by Hydrophilic-Interatction Liquid Chromatography-Electrospray Tandem Mass Spectrometry, Clinical Chemistry 2006, Bd. 52, Nr. 3, S. 488-493.

Prospekt Method Development Guide for Hypercarb Columns der Firma Thermo Electron Corporation.

Jens Martens-Lobenhoffer and Stefanie M. Bode-Boger, Chromatographic-Mass Spectrometric Method for the Quantification of L-Arginine and its Methylated Metabolites in Biological Fluids, Journal of Chromatography, 2007 B, 851, S. 30-4.

Jens Martens-Lobenhoffer, Olga Krug and Stefanie M. Bode-Boger, Determination of Arginine and Asymmetric Dimethylarginine (ADMA) in Human Plasma by Liquid Chromatography/Mass Spectrometry with the Isotope Dilution Technique, Journal of Mass Spectrometry 2004, 39, 1287-1294.

Tadashi Ogawa, Masumi Komoto and Kei Sasaoka, Purification and Properties of a New Enzyme, N(G), N(G)- Dimethylarginine Dimethylaminohydrolase, from Rat Kidney, The Journal of Biological Chemistry 1989, 264, 10205-10209.

Vinod Achan, Michael Broadhead, Mohammed Malaki, Guy Whitley, James Leiper, Raymond Macallister and Patrick Vallance, Asymetric Dimethylarginine Causes Hypertension and Cardiac Dysfunction in Humans and Is Actively Metabolized by Dimethylarginine Dimethylaminohydrolase, Arteriosclerosis, Thrombosis, and Vascular Biology. 2003, 23:1455-49.

daCosta, Kerry-Ann et al "The Measurement of Dimethylamine, Trimethylamine, and Trimethylamine N-Oxide Using Capillary Gas Chromatography-Mass Spectrometry", Analytical Biochemistry 187, pp. 234-239 (1990).

Pettersson Anders, et al. "Determination of dimethylated arginines in human plasma by high-performance liquid chromatography", Journal of Chromatography B, 692 (1997), pp. 257-262.

DLD Diagnositka GmbH Company Profile.

\* cited by examiner

METHOD FOR DETERMINING THE CONCENTRATION OF ASYMMETRIC DIMETHYLARGININE (ADMA)

This is an application filed under 35 USC § 371 of PCT/DE2006/000829 filed May 13, 2006.

BACKGROUND OF THE INVENTION

The invention is directed to a method for determining the concentration of asymmetric dimethylarginine simultaneously with arginine and symmetric dimethylarginine (SDMA) in biological samples by HPLC-MS-MS.

In biological systems, the amino acid arginine represents, inter alia, a starting material for the synthesis of the messenger nitric oxide (NO) by the enzymes of the group of nitrogen monoxygenases (NOS). Sufficient availability of this messenger is also a prerequisite for the physiological function of the endothelial cells in the cardiovascular system, whereas a deficiency in NO is related to endothelial dysfunction and the associated disease states, such as arteriosclerosis, hypertension or stroke.

Arginine integrated in proteins is metabolized in the body on a further metabolic pathway via the enzyme group of the protein-methyl-transferases (PRMT) into monomethylarginine (MMA), asymmetric dimethylarginine (ADMA) and symmetric dimethylarginine (SDMA). These amino acids are released during enzymatic protein decomposition. The released methylated arginine derivatives MMA and ADMA inhibit the function of NOS and thereby reduce the production of NO. MMA plays hereby only a minor role, because its effective concentration attains only approximately 10% of that of ADMA. Although SDMA itself does not inhibit NOS, it shares with ADMA the transport mechanism through the cell membranes and can therefore indirectly affect the generation rate of NO.

Elevated plasma levels of ADMA are described in a number of disease states, such as hypertension, hypercholesterolemy, kidney failure or diabetes mellitus, and it can be safely assumed that an elevated plasma level of ADMA is a direct risk factor for cardiovascular diseases.

For investigating these diseases and therapeutic approaches, a steadily increasing demand for the determination of ADMA in different biological fluids, such as blood plasma, urine or a cell culture medium, can be expected.

ADMA is excreted in biological systems both through the kidney in unchanged form or enzymatically divided into citrulline and dimethylamine. This means that ADMA and SDMA increase in the blood in patients with kidney failure. A kidney transplant normalizes the SDMA level, but lowers the ADMA level only slightly, because dimethylamine-dimethylamino hydrolase (DDAH) becomes the main metabolization pathway for ADMA (SDMA is not metabolized). Two isoforms exist: DDAH I has been found in tissue with neuronal NOS, whereas DDAH II is found in tissue with endothelial NOS. A number of pathological stimuli increase oxidative stress, such as oxidized LDL-cholesterol, cytokine, hyperhomocysteinemy, or hyperglycomy. Each of these stimuli cause a decrease in the DDAH activity due to increased formation of oxygen radicals and hence an increase in the ADMA concentration, as depicted in the Figure illustrating the prior art. This effect can be compensated in vitro through administration of antioxidants, restoring the DDAH activity.

The activity of DDAH is of considerable importance for the equilibrium concentration of ADMA in biological systems. It is known that the activity of DDAH is affected by external factors, such as oxidative stress. A decreased activity causes increased ADMA levels with their negative consequences.

The quantitative measurement of ADMA in biological samples is made more difficult because, in addition to ADMA, a large number of other constituents are present in these samples, wherein the other physiological amino acids and in particular SDMA which has a structure similar to that of ADMA make a quantitative determination difficult. A number of methods for determining ADMA in biological samples are generally known from the published literature. Most widely used is the method of high pressure-liquid chromatography with fluorescence detection. Arginine, ADMA, SDMA, optionally MMA and an internal standard, are hereby extracted from biological samples by ion exchange-solid phase extraction (SPE), the extract is reacted with orthophthalic aldehyde and a mercaptan (e.g., 2-mercaoptoethanol, 3-mercaptopropionic acid) to form a fluorescing derivate; the derivates of the aforementioned compounds are separated with HPLC and quantitatively measured using fluorescence detection. A large number of modifications of this method have been described (see, for example, Chen B M, Xia L W, Zhao R Q. Determination of N(G),N(G)-dimethylarginine in human plasma by high-performance liquid chromatography. J Chromatogr B Biomed Sci Appl 1997; 692: 467-71, Meyer J, Richter N, Hecker M. High-performance liquid chromatographic determination of nitric oxide synthase-related arginine derivatives in vitro and in vivo. Anal Biochem 1997; 247: 11-6, Pettersson A, Uggla L, Backman V. Determination of dimethylated arginines in human plasma by high-performance liquid chromatography, J Chromatogr B Biomed Sci Appl 1997; 692: 257-62, Pi J, Kumagai Y, Sun G, Shimojo N. Improved method for simultaneous determination of L-arginine and its mono- and dimethylated metabolites in biological samples by high-performance liquid chromatography, J Chromatogr B Biomed Sci Appl 2000; 742: 199-203, Dobashi Y, Santa T, Nakagomi K, Imai K. An automated analyzer for methylated arginines in rat plasma by high-performance liquid chromatography with post-column fluorescence reaction. Analyst 2002; 127: 54-9, Teerlink T, Nijveldt R J, de Jong S, van Leeuwen PAM. Determination of arginine, asymmetric dimethylarginine, and symmetric dimethylarginine in human plasma and other biological samples by high-performance liquid chromatography. Anal Biochem 2002; 303:131-7, Marra M, Bonfigli A R, Testa R, Testa I, Gambini A, Coppa G. High-performance liquid chromatographic assay of asymmetric dimethylarginine, symmetric dimethylarginine, and arginine in human plasma by derivatization with naphthalene-2,3-dicarboxaldehyde. Anal Biochem 2003; 318: 13-7 Heresztyn T, Worthley M I, Horowitz J D. Determination of 1-arginine and N(G), N(G)- and N(G), N(G')-dimethyl-1-arginine in plasma by liquid chromatography as AccQ-Fluor™ fluorescent derivatives. J Chromatogr B AnalytTechnol Biomed Life Sci 2004; 805: 325-9 and Zhang W Z, Kaye D M. Simultaneous determination of arginine and seven metabolites in plasma by reversed-phase liquid chromatography with a time-controlled ortho-phthaldialdehyde precolumn derivatization. Anal Biochem 2004; 326: 87-92). A major disadvantage of this method is the extraction with SPE, which is labor intensive, expensive and error prone. Other chromatographic separation methods are based on capillary electrophoresis with fluorescence detection (see, for example, Causse E, Siri N, Arnal J F, Bayle C, Malatray P, Valdiguie P et al. Determination of asymmetrical dimethylarginine by capillary electrophoresis-laser-induced fluorescence. J Chromatogr B Biomed Sci Appl 2000; 741: 77-83, und Trapp G, Sydow K, Dulay M T, Chou T, Cooke J P, Zare R N. Capillary electrophoretic and micellar electrokinetic separations of asymmetric dimethyl-L-arginine and structurally related amino acids: quantitation in human plasma. J Sep Sci 2004; 27: 1483-90), or gas chromatography with mass-spectrometric detection after a corresponding extraction and derivatization of ADMA and optionally arginine and SDMA (see, for example, Tsikas D, Schubert B, Gutzki F M, Sandmann J, Frolich J C. Quantitative determination of circulating and urinary asymmetric dimethylarginine (ADMA) in humans by gas chromatography-tandem mass spectrometry as methyl ester tri(N-pentafluoropropionyl) derivative. J Chromatogr B AnalytTechnol Biomed Life Sci 2003; 798: 87-99 and Albsmeier J, Schwedhelm E, Schulze F, Kastner M, Boger R H. Determination of N(G),N(G)-dimethyl-I-arginine, an endogenous NO synthase inhibitor, by gas chromatography-mass spectrometry. J Chromatogr B AnalytTechnol Biomed Life Sci 2004; 809: 59-65). Newer methods applying the HPLC-MS technology have also been described (see Huang L F, Guo F Q, Liang Y Z, Li B Y, Cheng B M (2004) Simultaneous determination of L-arginine and its mono- and dimethylated metabolites in human plasma by high-performance liquid chromatography-mass spectrometry. Anal Bioanal Chem 380: 643-649, Martens-Lobenhoffer J, Krug O, Bode-Boger S M (2004) Determination of arginine and asymmetric dimethylarginine (ADMA) in human plasma by liquid chromatography/mass spectrometry with the isotope dilution technique. J Mass Spectrom 39:1287-1294; Kirchherr H, Kuhn-Velten W N (2005) HPLC-tandem mass spectrometric method for rapid quantification of dimethylarginines in human plasma. Clin Chem 51:249-252, and Schwedhelm E, Tan-Andresen J, Maas R, Riederer U, Schulze F, Boger R H (2005) Liquid chromatography-tandem mass spectrometry method for the analysis of asymmetric dimethylarginine in human plasma. Clin Chem 51:1268-1271). These methods partially require derivatization of the analytes prior to chromatography or require complete chromatographic separation of ADMA and SDMA for obtaining reliable quantitative results. A basically different approach for determining of ADMA in biological samples is the determination through immunological reactions using specific antibodies. Commercially available reagent kits operate according to the ELISA process (enzyme-linked immunosorbent assay). However, this process is in principle only capable of quantifying a single analyte, in this case ADMA. Unlike with chromatographic methods, a simultaneous determination of, for example arginine or SDMA, is not possible.

BRIEF SUMMARY OF THE INVENTION

It is an object of the invention to obviate the disadvantages of conventional processes for determining the concentration of asymmetric dimethylarginine (ADMA) simultaneously with arginine and symmetric dimethylarginine (SDMA) in biological samples with HPLC-MS-MS. It is also an object of the invention to develop a cost-effective method for routine processing of large sample quantities with accurate results.

The object is attained with the invention by a method for determining the concentration of asymmetric dimethylarginine (ADMA) simultaneously with arginine and symmetric dimethylarginine (SDMA) in biological samples by using HPLC-MS-MS, characterized in that the sample preparation includes only the addition of a solution of an isotope-marked internal standard ($^{13}C_6$-arginine and $D_6$-ADMA) and the addition of a mixture of acetonitrile/propionic acid/trifluoroacetic acid for a precipitation of high-molecular proteins, whereby quantity and composition are realized by adjusting the sample composition to match the composition of the mobile phase in the HPLC separation, without requiring derivatization or extraction of the analytes, that chromatographic separation of the analytes occurs on a silica normal phase HPLC column by using a mobile phase of water/acetonitrile/propionic acid/trifluoroacetic acid, wherein the volume ratio of water to acetonitril is from 2 to 98 to 30 to 70, the volume fraction of trifluoroacetic acid is 0.01 to 0.5, the volume fraction of propionic acid is 10 to 100 times higher than that of trifluoroacetic acid, and that the optimized composition of the mobile phase is composed of water/acetonitrile/propionic acid/trifluoroacetic acid with 10/90/1/0.025 parts per volume, and the detection and quantification occurs via tandem mass spectrometry, wherein a fragmentation of 175.2 m/z→70.1 m/z for arginine, 181.2 m/z→74.1 m/z for $^{13}C_6$-arginine, 203.2 m/z→172.1 m/z for SDMA, 203.2 m/z→46.1 m/z for ADMA, and 209.2 m/z→70.1 m/z for $D_6$-ADMA is observed.

Advantageously, the afore described method for measuring arginine, ADMA and SDMA requires only a minimum of sample preparation. A labor-intensive, expensive and somewhat unreliable sample extraction via SPE is hereby completely eliminated, as is the derivatization of the analytes before chromatographic separation. A further innovation is the chromatographic separation of the analytes from the matrix components on a very inexpensive normal phase separation column (silica) with a 10/90/1/0.025 mixture of water/acetonitrile/propionic acid/trifluoroacetic acid as the mobile phase. Under these conditions, extremely polar substances can be separated quickly without prior derivatization, whereas practically no retention can be attained with conventional reverse-phase separation columns. A complete chromatographic separation of ADMA and SDMA is no longer necessary, because ADMA and SDMA can be completely differentiated based on their MS-MS spectra with a tandem mass spectrometer as detector. Compared to conventional methods with fluorescence detection, mass-spectrometric detection has the additional advantage that interferences and hence quantification errors can be practically eliminated due to the extremely high selectivity. The use of isotope-marked internal standards produces quantification with very high accuracy and correctness, independent of the sample matrix. Uncontrollable systematic errors which are observed when biological samples are measured with conventional methods, are completely eliminated. This applies also for the quantification of ADMA with ELISA-kits. The only commercially available ADMA-ELISA-kit (DLD Diagnostika GmbH, Germany) must be calibrated separately for each sample matrix (e.g., blood plasma, blood serum, cell culture medium). Moreover, the results depend, as confirmed by all or control measurements, on the corresponding disease type even for an otherwise identical sample matrix. Furthermore, the ELISA process is in principle only capable of determining a single analyte. Arginine and SDMA must then be quantified by using another method, before a meaningful overall picture regarding the NO-status of the biological system can be created by taking into account other clinical parameters, such as endothelial function. With the proposed analytical method, arginine, ADMA and SDMA can be determined simultaneously.

The investigation of cardiovascular diseases requires determination of arginine, ADMA and SDMA in the blood plasma of patients and in cell culture media. There is an ever increasing number of private biochemical laboratories which routinely offer such analyses. Therefore, there is also great interest in cost-effective, less labor-intensive and accurate analytical methods. The method of the invention described herein satisfies these requirements.

The invention will now be described in more detail with reference to an exemplary embodiment. The appended drawings show in:

BRIEF DESCRIPTION OF THE DRAWINGS

FIG. 1A: Illustrates Prior Art

FIG. 1B: a typical chromatogram for blood plasma, and in

The sample preparation for the quantitative analysis of arginine, ADMA and SDMA consists of only two steps which can be performed quickly and easily. In a first step, the sample (blood plasma, urine or cell culture medium) is mixed with a solution of the isotope-marked internal standards $^{13}C_6$-arginine (commercially available) and $D_6$-ADMA (produced according to Martens-Lobenhoffer J, Krug O, Bode-Boger SM (2004) Determination of arginine and asymmetric dimethylarginine (ADMA) in human plasma by liquid chromatography/mass spectrometry with the isotope dilution technique. J Mass Spectrom 39:1287-1294). In the second step, 9 parts of a mixture of acetonitrile/propionic acid/trifluoroacetic acid 99/1/0.025 (parts per volume) are added. The proteins in the sample are hereby precipitated and can be separated by centrifugation. The composition of the sample then also approaches that of the carrier (see below) for the HPLC separation, so that the chromatographic separation is not adversely affected by injection of samples with an elution potential different from that of the mobile phase. The samples prepared in this manner are directly supplied for HPLC separation. Separation takes place on a silica normal phase column, whereby the mobile phase does not employ a typical normal phase carrier (such as hexane or dichloromethane), but instead consists of a mixture of water/acetonitrile/propionic acid/trifluoroacetic acid. The volume ratio of water to acetonitrile can hereby have values from 2 to 98 to 30 to 70 parts per volume, whereby a larger water fraction results in shorter retention times and decreased separation efficiency.

Figure 1:
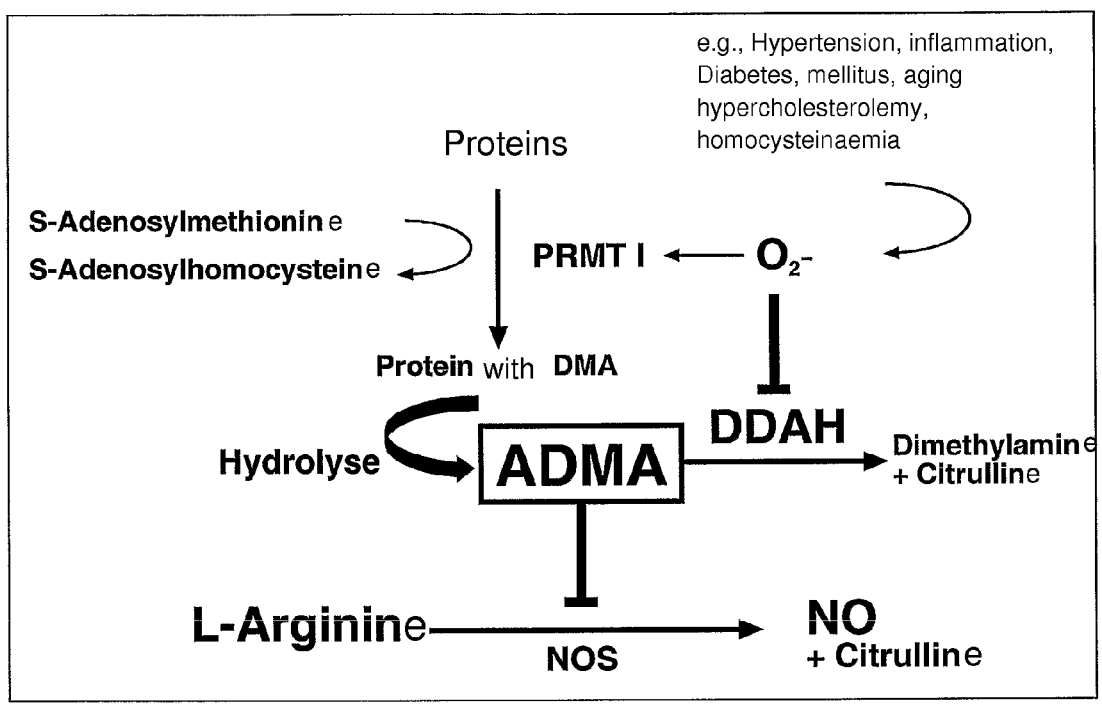
Figure 1:
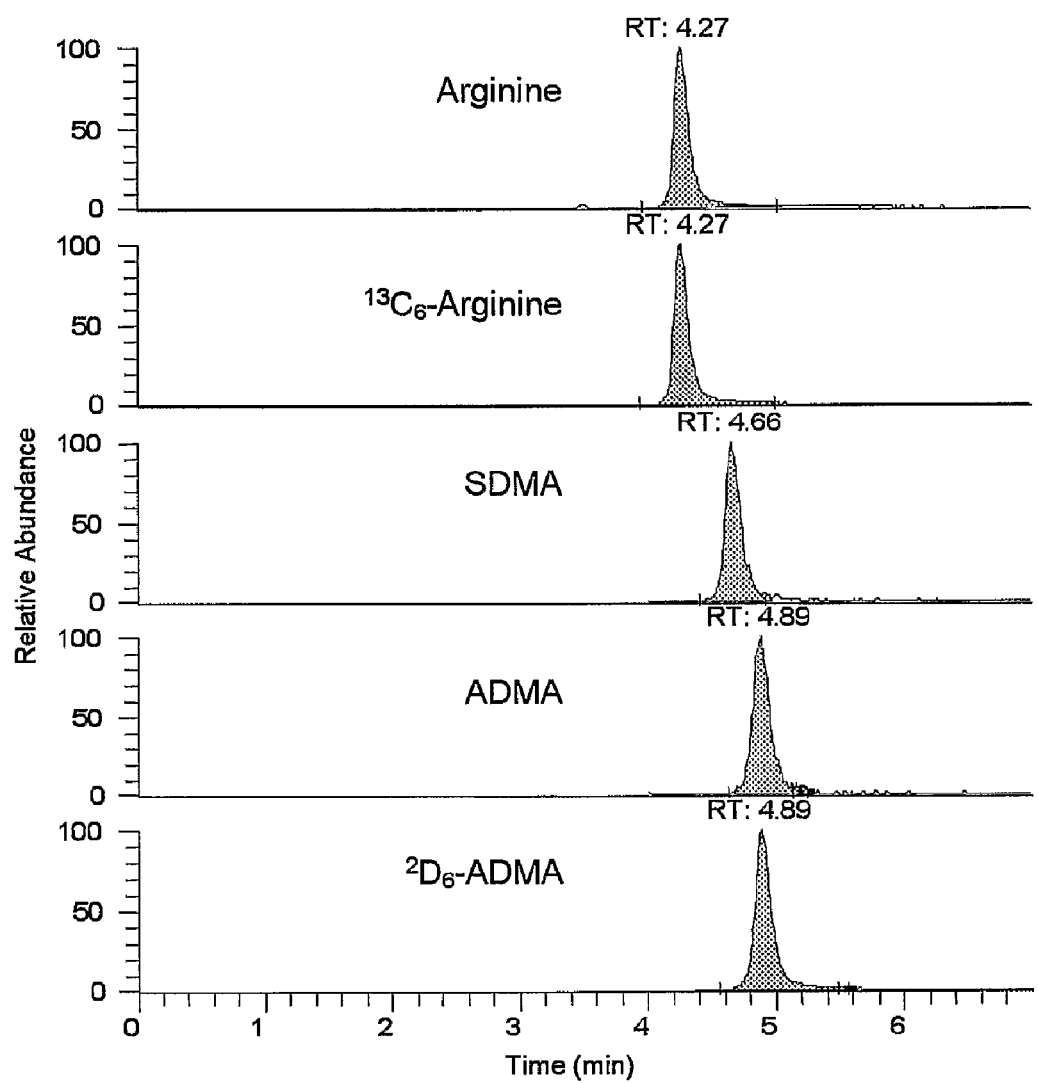

Trifluoroacetic acid with a concentration of 0.01 to 0.5 parts per volume in the carrier produces sharp and symmetric peaks in the chromatogram, whereas a simultaneously present 10 to 100 times higher fraction of propionic acid in the carrier compensates for the decrease in the ionization yield in the mass spectrometric detector caused by the trifluoroacetic acid. The optimized volume ratios of water/acetonitrile/propionic acid/trifluoroacetic acid are 10/90/1/0.025. Under these conditions, symmetric and sharp peaks are obtained which are completely separated from the matrix components (see FIG. 1).

The analytes are detected by tandem mass spectrometry after positive ionization in an electrospray ion source. The following fragmentations are observed: 175.2 m/z→70.1 m/z for arginine, 181.2 m/z→74.1 m/z for $^{13}C_6$-arginine, 203.2 m/z→172.1 m/z for SDMA, 203.2 m/z→46.1 m/z for ADMA, and 209.2 m/z→70.1 m/z for $D_6$-ADMA. These ion-specific traces are selective for the afore described analytes, so that for the first time there is no longer a need for a complete chromatographic separation of ADMA and SDMA.

Quantification is done by using the ratio of the areas between analyte and internal standard. $^{13}C_6$-arginine is used as internal standard for arginine, and $D_6$-ADMA is used as internal standard for ADMA and SDMA.

Validation of this method yields good results for all described biological fluids. The various data are summarized in Table I. The accuracy of consecutive measurements was determined by measuring a sample 10 times during a work shift, the repeat accuracy by measuring a sample six times on different days.

TABLE I

| Substance | Medium | Calibration region (μmole/l) | Accuracy of consecutive measurements (%) | Repeat accuracy (%) |
|---|---|---|---|---|
| arginine | blood plasma | 0-150 | 4.48 | 4.66 |
| | urine | 0-50 | 4.09 | 4.76 |
| | cell culture medium | 0-50 | 4.59 | 2.92 |
| ADMA | blood plasma | 0-3 | 5.52 | 7.67 |
| | urine | 0-100 | 2.51 | 5.36 |
| | cell culture medium | 0-3 | 3.40 | 7.68 |
| SDMA | blood plasma | 0-4 | 3.93 | 4.86 |
| | urine | 0-100 | 2.93 | 5.18 |
| | cell culture medium | 0-4 | 10.8 | 6.48 |

Figure 2:
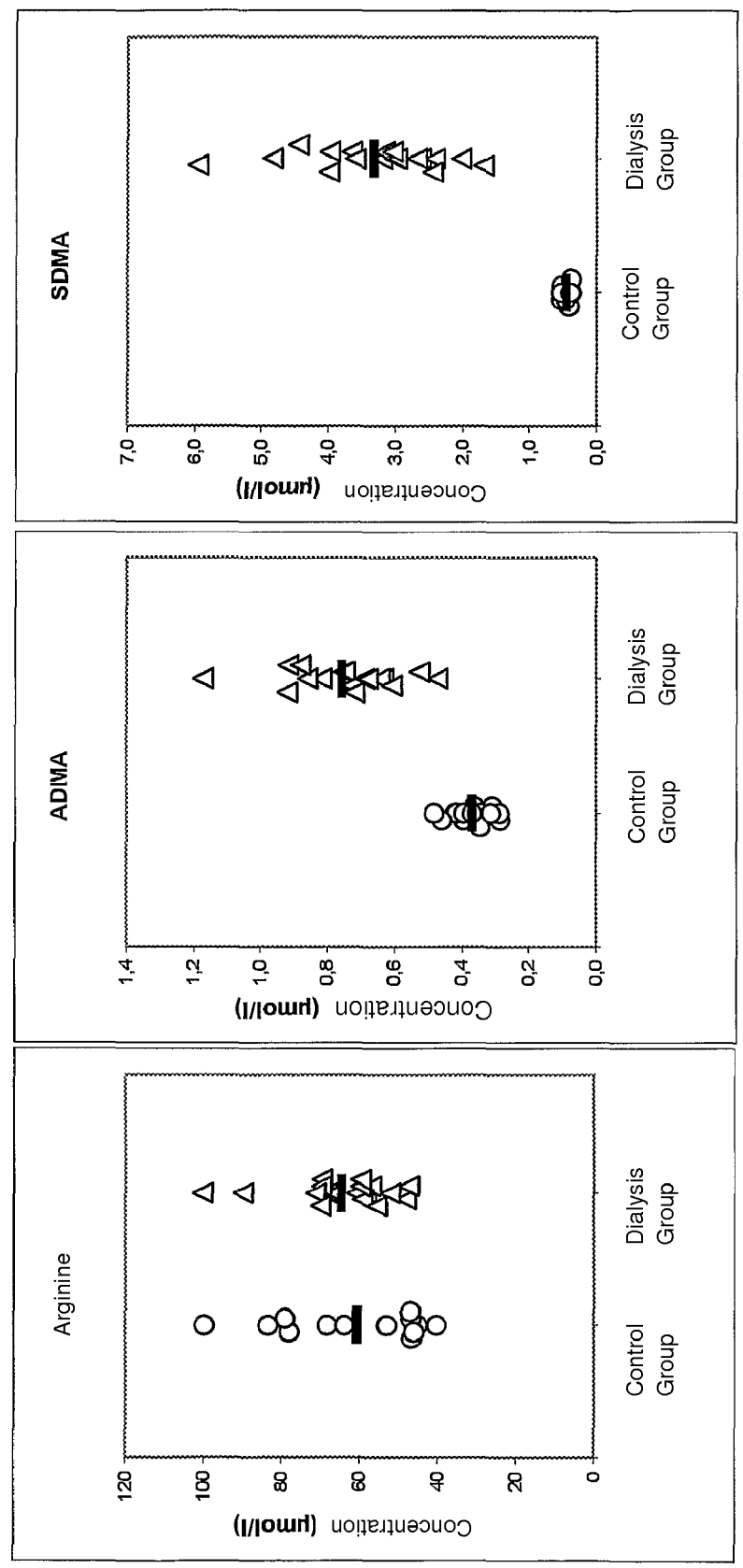
FIG. 2: blood plasma values for arginine, ADMA and SDMA of normal subjects and patients required to undergo dialysis.

Blood plasma values for arginine, ADMA and SDMA of normal subjects and dialysis patients were determined in a clinical research environment (FIG. 2). It is evident that the values for ADMA and SDMA in the group of dialysis patients were significantly much greater than those in the control group, whereas no significant difference was found for arginine. The median value for arginine is 60.6±18.27 μmole/l in the control group and 64.5±13.41 μmole/l in the dialysis group. The corresponding values for ADMA are 0.370±0.061 μmole/l compared to 0.757±0.165 μmole/l, and for SDMA 0.449±0.055 μmole/l compared to 3.308±1.048 μmole/l.

The invention claimed is:

1. A method for determining the concentration of asymmetric dimethylarginine (ADMA) simultaneously with arginine and symmetric dimethylarginine (SDMA) in biological samples by using HPLC-MS-MS, comprising the steps of preparing a sample including only addition of a solution of isotope-marked internal standards ($^{13}C_6$-arginine and $D_6$-ADMA) and addition of a mixture of acetonitrile/propionic acid/trifluoroacetic acid for precipitation of high-molecular proteins, whereby quantity and composition are realized by adjusting the sample composition to the composition of the mobile phase in the HPLC separation, without requiring derivatization or extraction of the analytes, separating chromatographically the analytes occurring on a silica normal phase HPLC column by using a mobile phase of water/acetonitrile/propionic acid/trifluoroacetic acid, wherein the volume ratio of water to acetonitril is from about 2 to 98 to 30 to 70, the volume fraction of trifluoroacetic acid is about 0.01 to 0.5, the volume fraction of propionic acid is about 10 to 100 times higher than that of trifluoroacetic acid, and the optimized composition of the mobile phase is composed of water/acetonitrile/propionic acid/trifluoroacetic acid with about 10/90/1/0.025 parts per volume, and the detection and quantification occurs by a tandem mass spectrometry, wherein the fragmentation is about 175.2 m/z→70.1 m/z for arginine, about 181.2 m/z→74.1 m/z for $^{13}C_6$-arginine, about 203.2 m/z→172.1 m/z for SDMA, about 203.2 m/z→46.1 m/z for ADMA, and about 209.2 m/z→70.1 m/z for $D_6$-ADMA.

2. The method according to claim 1, wherein the sample matrix is blood plasma.

3. The method according to claim 1, wherein the sample matrix is urine.

4. The method according to claim 1, wherein the sample matrix is a cell culture medium.

* * * * *